United States Patent [19]

Whitesides et al.

[11] 4,164,444
[45] Aug. 14, 1979

[54] METHOD FOR PREPARING ADENOSINE TRIPHOSPHATE

[75] Inventors: George M. Whitesides, Newton; Patricia E. Garrett, Somerville, both of Mass.; Merrell G. Siegel, Houston, Tex.

[73] Assignee: Massachusetts Institute of Technology, Cambridge, Mass.

[21] Appl. No.: 764,516

[22] Filed: Jan. 31, 1977

Related U.S. Application Data

[62] Division of Ser. No. 666,995, Mar. 15, 1976, Pat. No. 4,088,675.

[51] Int. Cl.$^2$ .................. C12D 13/06; C07H 19/20
[52] U.S. Cl. ................... 435/92; 260/501.2; 260/545 P; 260/987; 536/27; 536/28; 536/29
[58] Field of Search .................. 536/27, 28, 29; 195/28 N

[56] References Cited

U.S. PATENT DOCUMENTS

| 3,079,379 | 2/1963 | Tanaka et al. | 536/27 |
| 3,188,309 | 6/1965 | Mukaiyama et al. | 536/27 |
| 3,188,310 | 6/1965 | Mukaiyama et al. | 536/27 |
| 3,321,463 | 5/1967 | Moffatt | 536/27 |
| 3,594,278 | 7/1971 | Naylor | 195/28 N |
| 3,779,867 | 12/1973 | Katoh et al. | 195/28 N |
| 3,878,194 | 4/1975 | Moffatt et al. | 536/27 |

Primary Examiner— Brown
Attorney, Agent, or Firm—Arthur A. Smith, Jr.; David G. Conlin

[57] ABSTRACT

Acyl phosphate salts suitable for use as phosphate donors in the production of cofactors, such as adenosine triphosphate, are prepared by acylation of phosphoric acid with a ketene, followed by reaction with ammonia or an amine. The reaction product, e.g. diammonium acetyl phosphate, can normally be used directly in enzymic production of cofactors without the necessity of prior conversion to the free acid or another salt, such as the sodium salt. The acyl phosphate salts are produced in high yields, and the method allows production of cofactors for use in biosynthesis from readily available materials.

10 Claims, No Drawings

METHOD FOR PREPARING ADENOSINE TRIPHOSPHATE

The Government has rights in this invention pursuant to Grant No. APR 72-03424 and IPA-0010 awarded by the National Science Foundation This is a division, of application Ser. No. 666,995 filed Mar. 15, 1976, now U.S. Pat. No. 4,088,675, issued May 9, 1978.

BACKGROUND OF THE INVENTION

This invention deals with the preparation of salts of acyl phosphoric acids, more particularly with the preparation of ammonium salts of acyl phosphates, such as diammonium acetyl phosphate. Such compounds are useful in the production of phosphorylating agents such as adenosine triphosphate (ATP), a required cofactor in many reactions in the biosynthesis of materials such as protein, carbohydrates, nucleotides, nucleic acids, and terpenes. The products of the present invention can also be used as phosphorylating agents themselves or as acylating agents, e.g. diammonium acetyl phosphate reacts with aniline to form acetanilide in aqueous media at room temperature.

Biosynthesis by enzymatic catalysis has been attracting increased attention as a means of large scale production of many complex products. See, e.g., Skinner, "Enzymes Technology," *Chem. & Engin. News*, Vol. 53, No. 33, p. 22 (Aug. 18, 1975). A major limitation on the commercial usefulness of such processes, however, has been the cost of many of the cofactors or coenzymes necessary to conduct the reactions involved. For example, ATP is a cofactor which plays a prominent role in many biosynthetic processes, promoting formation of chemical bonds which otherwise would not form in significant quantities in dilute aqueous solutions. See generally Stadtman, "The Enzymes", Vol. 8, chapter 1 (3rd ed. 1972). For the use of ATP in cell-free enzymatic synthesis of the cyclic decapeptide antibiotic Gramicidin S, see Gardner et al., *Enzyme Engineering* 2:209 (1974); Whitesides et al., *Enzyme Engineering* 2:217 (1974); and Hamilton et al., *Enzyme Engineering* 2:133 (1974), all incorporated herein by reference. The cost of cofactors such as ATP is extremely high (reported by Skinner, supra, at $67 per gram), which has severely retarded the use of such processes on a commercial scale.

In order to reduce the cost of enzymatic synthesis requiring ATP, a system has been developed by enzymatic regeneration of ATP from adenosine diphosphate (ADP) and/or adenosine monophosphate (AMP). Normally treatment of the raw materials used in biosynthesis with ATP to form more complex products results in the consumption of ATP and the production of AMP and/or ADP. Under the regeneration system, if AMP is produced in the biosynthesis, it is converted to ADP by enzyme catalyzed phosphoryl transfer from ATP according to the following equation:

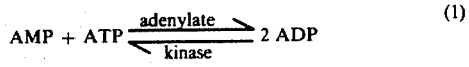
(1)

The ADP is then converted to ATP by reaction with a phosphate donor, e.g. acetyl phosphate (AcP), catalyzed by a phosphotransferase enzyme, e.g. acetate kinase:

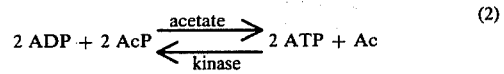
(2)

Whitesides et al., supra, and Gardner et al., supra, both discuss this regeneration scheme. While this significantly reduced the difficulty in obtaining ATP, it did not eradicate it, largely because commercially acceptable methods of producing the phosphate donors such as acetyl phosphate were not known.

Acetyl phosphate had previously been synthesized from phosphoric acid by acylation with various ingredients, including acetyl chloride, ketene, isopropenyl acetate, and acetic anhydide, followed by isolation as the lithium or silver salts. See Whitesides et al., "Large-Scale Synthesis of Diammonium Acetyl Phosphate," *J. Org. Chem.*, 40:2516 (1975) and references cited, incorporated herein by reference. All of these procedures involve difficult work-up and isolation sequences, and none of them are suitable for the preparation of acetyl phosphate in large quantity.

The previously known processes of producing acetyl phosphate by acylation of phosphoric acid with ketone are discussed in Whitesides et al., supra, and in Bently, "A New Synthesis of Acetyl Dihydrogen Phosphate," *J. Amer. Chem. Soc.* 70:2183 (1948). See also Kasalopoff et al., "Organic Phosphorous Compounds," Vol. 6:294, at 295-6 (1973). Generally, ketene, obtained for example from the cracking of acetic acid or acetone, was reacted with 85% phosphoric acid dissolved in ether to produce a mixture of monoacetyl, diacetyl and triacetyl phosphates, depending on factors such as concentrations of the reactants and the length of reaction, together with other reaction products. The acetyl phosphates were then isolated either as the silver salts or as the lithium salts. Isolation as the silver salt involved an ice water wash, precipitation of unreacted phosphate with barium hydroxide, and treatment of the remaining barium acetyl phosphate solution with excess ice-cold silver nitrate. The disilver acetyl phosphate would then be converted into acetyl phosphate by treatment with hydrogen sulfide in aqueous solution, or by suspension in ether and treatment with ethereal hydrogen chloride. The disilver acetyl phosphate could also be converted to diammonium acetyl phosphate, first by converting the silver salt to the free acid in ether, followed by reaction with dry ethereal ammonia. See Bently, supra, at 2183-4. Isolation as the dilithium salt involved neutralization with aqueous lithium acetate, carbonate or hydroxide. Dilithium acetyl phosphate was then precipitated by addition of ethanol. It was then necessary to remove water from the dilithium acetyl phosphate without hydrolyzing it. Following this procedure acyl phosphate was obtained in yields of about 50%, based on the starting phosphoric acid.

Clearly, these previous procedures for preparing usable acetyl phosphate were very difficult as best. They require a neutralization step of the acetyl phosphoric acid in aqueous solutions, followed by the use of very expensive silver or lithium salts to effect isolation of the acetyl phosphate. Neutralization with the lithium salts, e.g. lithium acetate, carbonate or hydroxide, results in phosphate "slimes", through which it is difficult to separate the mother liquor. Removal of water from dilithium acetyl phosphate without hydrolyzing it required a time consuming and not always successful lyophilization or related procedure. Yields were relatively low, and the silver salt had to be converted to the sodium, potassium, or other salt before it could be used to regenerate ATP.

Accordingly, it is an object of the present invention to provide a simple, direct method of producing acyl phosphates. It is a further object to provide a simple, inexpensive method of producing phosphate donors suitable for use in biosynthesis. It is a more particular object to provide a method of producing phosphate donors useful in production of ATP. It is a further object to provide a process for making ATP utilizing ammonium acyl phosphates, more particularly diammonium acetyl phosphate. It is a further object of this invention to provide a process of preparing acyl phosphates in high yield, without the need for expensive lithium or silver precipitation. It is a still further object to provide a method of preparing acyl phosphate salts which are highly stable, and can be used directly as a phosphate donor, without having to be converted to dihydrogen acyl phosphate, more particularly, the ammonium acyl phosphate salts. It is a still further object to provide a method of preparing acetyl phosphate salts, more particularly diammonium acetyl phosphate, which is efficient and economical enough for use on an industrial scale.

Further objects of the invention will be apparent to those skilled in the art from a consideration of the present disclosure, and/or from practice of the invention disclosed herein.

BRIEF SUMMARY OF THE INVENTION

Basically, the invention involves production of acyl phosphate salts by a process which includes acylation of phosphoric acid by a ketene, followed by precipitation of the acyl phosphate as an ammonium salt or a salt of certain organic bases discussed below. The acylation is performed in a suitable solvent, preferably water free, since if there is water present the loss of some ketene to production of acids or anhydrides will occur. Generally, the acylation reaction will result in a mixture of monoacyl phosphate with diacyl phosphate and/or triacyl phosphate. However, in the present process the presence of excess ammonia apparently converts the diacyl phosphate and triacyl phosphate into the monoacyl phosphate salt. After completion of the acylation reaction, the reaction mixture is preferably diluted with a solvent in which the desired ammonium acyl phosphate salt is either insoluble or only sparingly soluble, such as methanol in the case of diammonium acetyl phosphate, and then treated with anhydrous ammonia. The ammonium acyl phosphate precipitates out and is separated from the mother liquor. The products of the acylation reaction can also be first treated with the anhydrous ammonia to form the ammonium salt, and the salt can be separated from the reaction mixture by dilution with the non-solvent for that salt. The reaction scheme may be depicted as follows:

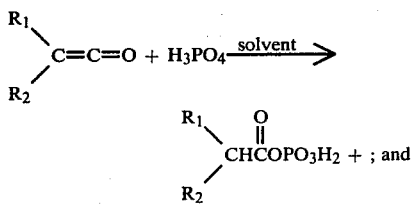

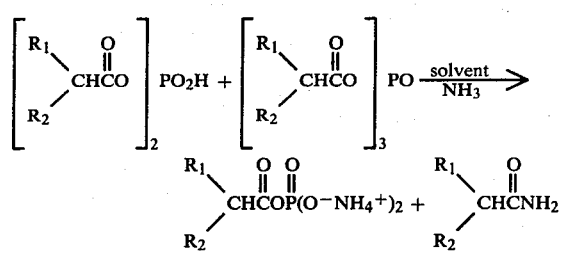

wherein $R_1$ and $R_2$ may be hydrogen, alkyl, aryl, aralkyl or alkaryl. Preferably $R_1$ and $R_2$ are selected from hydrogen, lower alkyl of $C_{1-5}$ and phenyl. $R_1$ and $R_2$ may be the same or may be different, but if neither is hydrogen they are preferably the same. Suitable ketenes include ketene ($CH_2=C=O$), methyl ketene, dimethyl ketene, diethyl ketene, diphenyl ketene, etc. Ketene itself is most preferred, since it is a relatively cheap industrial chemical which is readily available from the pyrolysis of acetone, and is highly reactive.

Both reactions are preferably carried out at low temperatures with a broadly suitable range being $-30°$ to $30°$ or $35°$ C. Preferably the reaction is carried out at $-20°$ to $10°$ C., with the optimum yields being felt at about $-10°$ to $-0°$ C. Yield apparently falls off above $10°$ C. Presently preferred is about $0°$ C., largely because of the convenience of controlling the reaction temperature by a simple ice bath.

The solvent used in the acylation reaction should be one in which phosphoric acid is soluble, yet which does not react with the ketene used. A wide variety of ethers are suitable, such as the alkyl ethers, e.g., ethyl, n-propyl, n-butyl, etc. Compounds with more than one ether linkage, such as 1,2 dimethoxyethane, are suitable. Amides, such as formamide, dimethyl acetamide, are also suitable. Carboxylic acid esters, especially alkyl esters such as ethyl acetate, n-butyl acetate, etc., are also highly suitable. See generally Von Wazer, *Phosphorus and Its Compounds*, 2:482-3 (1958), and references cited therein. Presently preferred is ethyl acetate, which seems to consistently give the highest yields and the highest purity of product.

As indicated, water present in the reaction mixture reacts with the ketene to form biproducts such as acetic acid or acetic anhydride. The number of products that can be formed by reaction of ketene with phosphoric acid containing some water is actually quite large. Thus it is far preferred that the reaction mixture be devoid of water. Dioxane diphosphate can be used as an alternate for a source of phosphate but has to be prepared and dried in a separate step. Accordingly, 100% phosphoric acid is the starting material of choice. The preparation of 100% phosphoric acid by dehydration of 85% phosphoric acid may easily be accomplished, e.g. with phosphorus pentoxide. See, e.g., Bell, *Anal. Chem.* 19:97 (1947). While use of 85% phosphoric acid is not preferred, since it contains about 1 equivalent of water per equivalent of phosphoric acid and thus results in competition between phosphoric acid and water for the available ketene, surprisingly high yields have been obtained even with 85% phosphoric acid.

The optimum molar ratio of ketene to phosphoric acid as a reaction mixture depends on a number of factors, including the purity of the starting materials. Generally molar ratios of ketene to phosphoric acid may range from about 1:10 to 10:1. Preferably the ratio is from about 1:2 to about 3.5:1. Again, much depends on the water content of the phosphoric acid. With anhydrous phosphoric acid being used, the high efficiency is achieved at values for the molar ratio of ketene to phosphoric acid of from between about 0.75:1 to about 2.5:1. A highly preferable range of mole ratios for acetyl phosphate made using anhydrous phosphoric acid occurs between the mole ratio of 1.0–2.0, with the maximum conversion being about 90–95% yield of diammonium acetyl phosphate, and the optimum occurring at a mole ratio of ketene to phosphoric acid of about 1.7. Use of a molar ratio of ketene to 100% phosphoric acid of 2 or greater results in isolation of diammonium acetyl phosphate in somewhat lower yield. While not wishing to be bound by theory, this decrease in yield seems to reflect the fact that addition of ammonia to these reactions yields thick suspensions which are somewhat difficult to filter. The increased time spent in filtration may lead to loss of the diammonium acetyl phosphate through neucleophilic attack by ammonia. The use of 85% phosphoric acid, in addition to giving lower yield because of the presence of water as previously discussed, was also less convenient in that the optimum yield appeared to be at ratios of ketene to 85% phosphoric acid of 2:3 or higher, and the use of 85% phosphoric acid in these ratios also leads to thick suspensions requiring long filtration times.

As indicated, the use of ammonia to isolate the acetyl phosphate is greatly preferred for a number of reasons. First, ammonia is extremely cheap, not only compared to silver or lithium salt, but as compared to other suitable bases. Second, ammonium acyl phosphate salts, particularly diammonium acetyl phosphate, are very soluble in water, and the ammonium ion is innocuous to most (although not all) enzymes. Thus, diammonium acetyl phosphate can be used directly in the regeneration of ATP, without conversion back to the free acid or to other acetyl phosphate salts. Further diammonium acetyl phosphate has high storage and adequate solution stability. However, other basic materials can be used in place of the ammonia if desired. Suitable materials include other nitrogen-containing basic materials, such as primary, secondary or tertiary amines, either alkyl, such as methyl amine, dimethyl-amine, trimethyl-amine, or aryl amines, such as aniline.

In the event that the ammonium or other moity in the acetyl phosphate salt adversely affects the enzyme with which it is to be used, they can be changed to other cations; for example, it is possible to convert diammonium acetyl phosphate to disodium acetyl phosphate, e.g. by treatment with an ion exchange resin in sodium form. Similarly, the diammonium salt can be converted to the free acid by treatment with cationic ion exchange resin in the acid form.

The solvent used in the second reaction should be one which does not attack or be affected by acyl phosphates, and one in which the acyl phosphate salt which is the end product, e.g. diammonium acetyl phosphate, is insoluble or only sparingly soluble. A suitable solvent for use in the preparation of diammonium acetyl phosphate is methanol, which is also readily available and from which diammonium acetyl phosphate precipitates out as an easily filtered crystalline solid. Other suitable solvents include ethanol, n-propanol, isopropanol, n-butanol, as well as lower esters of lower acids, e.g. methyl acetate, ethyl acetate, lower alkyl formates, propionates, etc., and also lower alkyl ethers, e.g. ethyl ether, methyl-n-propyl ether, methyl tert butyl ether, etc.

Another novel aspect of this invention is the use of diammonium acetyl phosphate directly in production of ATP. This is done simply by mixing the diammonium acetyl phosphate and ADP together with acetate kinase and incubating at about room temperature until the reaction is complete. Suitable amounts of acetate kinase are about 700–2000 units, preferably about 1200–1600 units, and a suitable amount of adenylate kinase is about 200–1400 units, preferably about 600–800 units, per mole of diammonium acetyl phosphate regenerated per day. Of course, diammonium acetyl phosphate can be added to solutions containing AMP, with or without ADP originally, together with adenylate kinase, and the reactions will follow equations (1) and (2) above.

The invention will be further illustrated by the following illustrative embodiments.

EXAMPLE 1

Ethyl acetate (750 ml) and 100% phosphoric acid (100 grams 1.02 mol) were transferred into a 2 liter three-neck flask, fitted with a thermometer, gas inlet and outlet, and an overhead stirrer. The resulting solution was cooled to $-10°$ C. using an ethylene glycol/acetone/dry ice bath. Ketene was bubbled through the stirred solution for ten hours (1.98 mol), after which 750 ml of methanol, precooled to $-10°$ C., was added. Anhydrous ammonia, directly from the tank, was passed through aluminum coils, immersed in the cooling bath, then over the surface of the rapidly stirred solution, and finally out through a bubbler linked to the flask through the gas outlet. During this time, the internal temperature of the solution gradually rose to $-7°$ C. and then fell back to $-10°$ C., signaling the end of the reaction. A total of 65 grams of ammonia (3.82 mol) was then added to the reactants, although not all was necessarily consumed by the reaction mixture. The fine solid which filled the flask was collected by suction filtration, washed with methanol, ether, and contacted with methanol with magnetic stirring for ten minutes at room temperature, again washed with methanol and anhydrous ether, and then dried. Final drying to a constant weight under vacuum gave 180.2 grams of solid containing between 89% (enzymatic assay) and 91% (nmr assay) of diammonium acetyl phosphate, corresponding to a 91% yield based on phosphoric acid. The product should be stored at low temperature. Storage at 4° C. in a desiccator results in no decrease in purity over a period of two months, whereas storage in a desiccator for one month at 25° has resulted in a 30% decrease acetyl phosphate content. For further details, see Whitesides et al., "Large Scale Synthesis of Diammonium Acetyl Phosphate," *J. Org. Chem.* 40:2516 (1975).

EXAMPLE 2

In this example, diammonium acetyl phosphate produced in the manner of Example 1 was used to produce ATP by reaction with ADP, in accordance with equation number (2), supra. The production of ATP was confirmed by conversion of glucose to glucose-6-phosphate using the ATP produced from the diammonium acetyl phosphate, with catalysis by hexokinase, and then this glucose-6-phosphate was used to reduce nicotinamide adenine dinucleotide phosphate (NADP+) to NADPH, catalyzed by glucose-6-phosphate dehydrogenase. The equations involved are given in Whitesides et al., *supra*, Vol. 40, *J. Org. Chem.* at 2518. Under the conditions used, the equilibrium constants for each reaction lie far to the right, and thus the number of equivalents of NADPH produced is equal to the number of equivalents of diammonium acetyl phosphate added originally.

The following standard solutions were prepared.

Solution 1: To 300 mg of D-glucose and a mixture of 500 units of hexokinase and 250 units of D-glucose-6-phosphate dehydrogenase was added enough triethanol amine buffer (0.2 M, pH=7.6) containing magnesium chloride (0.03 M) to give 200 ml of solution.

Solution 2: Water was added to 250 mg of ADP (sodium salt) to give 1.0 ml of solution.

Solution 3: Water was added 330 mg of NADP+ (sodium salt) to yield 1.0 ml of solution.

Solution 4: Appoximately 70 mg of diammonium acetyl phosphate was brought to 10.0 ml with water.

The reaction was carried out as follows. To 5.0 ml of Solution 1 was added 0.05 ml of Solution 2, a 0.01 ml aliquot (ca 8.5 units) of a suspension of acetate kinase in 3.2 M ammonium sulfate solution and 0.05 ml of Solution 3. The solution was allowed to incubate at 25° until its absorbance, measured at 340 nm using a 1-cm cell, had reached a plateau, and this absorbance ($A_1$) was recorded. Another solution was prepared in the same manner, but to this solution was added 0.01 ml of Solution 4. The absorbence of the second solution ($A_2$) was then determined at 340 nm after a similar incubation. The absorbance $A_1$ corrects for the small amount of ATP present as a contaminant in the ADP, as well as any NADPH contaminant in the NADP+, and any other species which may have absorbance at 340 nm. This assay indicated that the product of Example 1 was about 89% diammonium acetyl phosphate by weight, with corresponds to a 91% yield based on the starting phosphoric acid.

EXAMPLE 3

This example illustrates the use of a base other than ammonia for isolating the acetyl phosphate.

To 150 ml of ethyl acetate was added 20 g of 100% phosphoric acid (0.204 mol). The solution was cooled to −10° C., and ketene was bubbled through the stirred solution for two hours. A 75 ml portion of this solution was withdrawn, and to the remainder was added 125 ml of precooled methanol, followed by the dropwise addition of 30 g of aniline (a 2.5-fold excess) over a period of ten minutes. During this time the internal temperature of the solution remained at −10° C. The resulting crystalline solid was collected by suction filtration, washed with acetone in ether, and dried. Enzymatic assay showed it to be 89.9% dianilinium acetyl phosphate.

EXAMPLE 4

This example illustrates the conversion of the diammonium acyl phosphate into other salts. This may be desirable, for example, in those relatively few instances where ammonium ions interfere to some degree with enzyme-catalyzed reactions. See Whitesides et al., *supra*, *J. Org. Chem.*, Vol. 40, at 2519, Note 10.

About 50 ml of Bio-Rad AG MP-50 ion exchange resin, a cation exchanger in hydrogen+ form containing sulfonic acid functional groups on a styrene-divinylbenzene copolymer lattice (100–200 mesh, about 1.86 meq/ml), manufactured by Bio-Rad Laboratories of Richmond, California, was washed three times by swirling in 150 ml of double-distilled water, allowing the suspension to settle and decanting the water and unsettled "fines". A 2-cm by 30-cm chromatography column was then filled with 40 ml of the washed resin, and 100 ml of sodium hydroxide (1.0 N) was slowly (1 ml/min) passed through it. This neutralization was followed by washing with 250 ml of water. The column was then transferred to a 4° C. cold room, allowed to equillibrate for two hours, and all following operations were carried out at 4° C. Doubly-distilled water was added to 1.0 g of diammonium acetyl phosphate prepared in accordance with Example 1, to make 4.0 ml of solution. This solution was placed on top of the ion exchange column. Doubly-distilled water was passed through the column at 1 ml/min, and 2.5 ml fractions were collected. The first 6 fractions had a pH of 4.5 and were devoid of acetyl phosphate. Fractions 7-14, however, having a pH of about 5.5, contained acetyl phosphate. These fractions, when combined, were found to contain 85% of the initial acetyl phosphate by enzymatic assay. However, an attempt at obtaining solid disodium acetyl phosphate from this solution was less successful. This solution was frozen lyophilized at 0.05 mm Hg, which resulted in 930 mg of white solid which was found to contain only 14% of the initial acetyl phosphate by enzymatic assay.

The specific embodiments described herein are meant to be exemplary only, and various modifications will be apparent to those skilled in the art. The claims below are intended to cover all such modifications that fall within the true spirit and scope of the invention.

We claim:

1. A method of preparing adenosine triphosphate in an enzyme-catalyzed reaction, said method comprising the step of reacting adenosine diphosphate in the presence of a phosphotransferase with an acetyl phosphate salt in which the cation is derived from the group of ammonia and primary, secondary and tertiary amines.

2. The method of claim 1, wherein the acetyl phosphate salt is diammonium acetyl phosphate.

3. The method of claim 2, in which the acetyl phosphate salt is dianilinium acetyl phosphate.

4. The method of claim 1, wherein the reaction is carried out by mixing adenosine diphosphate and the acetyl phosphate salt in the presence of acetate kinase.

5. The method of claim 4, wherein said adenosine diphosphate and said acetyl phosphate salt are mixed with from about 700 to about 2000 units of acetate kinase per mole of acetyl phosphate salt per day.

6. The method of claim 5, wherein said acetyl phosphate salt is diammonium acetyl phosphate.

7. The method of claim 4, wherein said acetyl phosphate salt is diammonium acetyl phosphate and said acetate kinase is present in an amount from about 1200 to about 1600 units per mole of diammonium acetyl phosphate per day.

8. The method of claim 1, wherein said reaction is carried out in the presence of adenylate kinase.

9. The method of claim 5, wherein said adenosine diphosphate and said acetyl phosphate salt are mixed with from about 200 to about 1400 units of adenylate kinase per mole of acetyl phosphate per day.

10. The method of claim 8, further comprising producing at least a portion of said adenosine diphosphate by reacting adenosine monophosphate in the presence of said adenylate kinase.

* * * * *